United States Patent [19]

Cardis et al.

[11] Patent Number: 5,126,063
[45] Date of Patent: Jun. 30, 1992

[54] BORATED HYDROXYALKYL ESTERS OF DITHIOCARBAMIC ACIDS AS MULTIFUNCTIONAL ADDITIVES FOR LUBRICANT COMPOSITIONS

[75] Inventors: Angeline B. Cardis, Florence; Liehpao O. Farng, Lawrenceville; Abraham O. M. Okorodudu, West Deptford; Andrew G. Horodysky, Cherry Hill, all of N.J.

[73] Assignee: Mobil Oil Corporation, Fairfax, Va.

[21] Appl. No.: 589,160

[22] Filed: Sep. 27, 1990

[51] Int. Cl.⁵ .................. C10M 139/00; C10M 135/18
[52] U.S. Cl. ..................... 252/46.3; 544/69; 546/13; 548/405; 558/236
[58] Field of Search .......................... 252/46.3; 544/69; 546/13; 548/405; 558/236

[56] References Cited

U.S. PATENT DOCUMENTS

| | | | |
|---|---|---|---|
| 3,407,222 | 10/1968 | Lies | 558/236 |
| 3,849,320 | 11/1974 | Bridger et al. | 252/33.6 |
| 4,104,181 | 8/1978 | Landis et al. | 252/46.7 |
| 4,859,356 | 8/1989 | Okorududu | 252/47.5 |
| 4,919,830 | 4/1990 | Farng et al. | 252/327 |

FOREIGN PATENT DOCUMENTS 0525670 8/1976 U.S.S.R.

Primary Examiner—Willis, Jr. Prince
Assistant Examiner—Jerry D. Johnson
Attorney, Agent, or Firm—Alexander J. McKillop; Charles J. Speciale; Jessica M. Sinnott

[57] ABSTRACT

Lubricating oil and grease compositions contain borated hydroxyalkyl esters of amine or metal salts of diorganodithiocarbamic acid, such as N,N'-di-(2-ethylhexyl) dithiocarbamic acid, and hydrocarbylene oxie, such as propylene oxide, as antioxidant, load-carrying and friction modifying additives.

26 Claims, No Drawings

BORATED HYDROXYALKYL ESTERS OF DITHIOCARBAMIC ACIDS AS MULTIFUNCTIONAL ADDITIVES FOR LUBRICANT COMPOSITIONS

FIELD OF THE INVENTION

This invention relates to lubricants. Specifically, the borated reaction products of amine or metal dithiocarbamate salts and organic oxides as multifunctional antioxidant, load carrying and friction modifying additives for blending with lubricants. Additionally, the invention relates to lubricant compositions containing the borated reaction products and methods of making the same.

BACKGROUND OF THE INVENTION

Under normal operating and storage conditions lubricants are subject to high temperatures and oxygen which leads to oxidation and decomposition of the lubricants. Oxidation of a lubricant can lead to the build-up of oil-soluble acids, lacquers and sludge which will cause serious damage to engines and other lubricated systems. Typically, antioxidant additives are blended with lubricants in order to improve the stability of the lubricants and thereby enhance the ability of the oil to resist oxidation.

Mechanical systems under heavy loads will deteriorate due to the frictional forces created by relatively moving, rubbing and bearing metal surfaces. Often, lubricants for such operations cannot prevent wear of the metal nor reduce the coefficient of friction and as a result the system performance is affected. Often, antiwear additives load carrying and friction modifying additives are blended with lubricants in order to prevent wear, reduce fuel consumption and increase the operating life of the machinery.

The metal salts of diorganodithiocarbamic acids have been described as multifunctional, antioxidant, antiwear and corrosion inhibiting additives for lubricants. However, these additives pose toxicological risks, thus, efforts are made to replace the metal salts with equally effective metal/phosphorus-free diorganodithiocarbamates.

The reaction products of diorganodithiocarbamic acids and alkylthiosulfinyl halides have been described as antioxidants and antiwear additives in lubricant compositions in U.S. Pat. No. 4,859,356 issued to Okorodudu.

SUMMARY OF THE INVENTION

It has now been found that the borated hydroxyesters derived from amine or metal dithiocarbamate salts and organic oxides are useful multifunctional antioxidant, load carrying and friction modifying additives for lubricating compositions.

The invention is directed to a reaction product for blending with a lubricant having multifunctional antioxidant, load carrying and friction modifying properties comprising the borated reaction product of an amine or metal dithiocarbamate salt and an organic oxide. A lubricating composition comprising a major amount of a lubricating oil or grease and a minor amount of a multifunctional antioxidant, load carrying and friction modifying borated reaction product of an amine or metal dithiocarbamic salt having the structural formula:

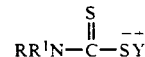

where R and R$^1$ are the same or different hydrocarbyl groups having at least 1 carbon atom and Y is a metal or ammonium radical with an organic oxide having the structural formula:

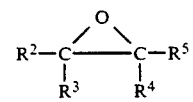

where R$^2$, R$^3$, R$^4$ and R$^5$ are the same or different, hydrogen or hydrocarbyl, containing at least 1 carbon atom or at least one heteroatom which can be oxygen, sulfur or nitrogen, and methods of making the same.

The esters of the present invention are formed from amine or metal salts of dithiocarbamic acids which have the following structural formula:

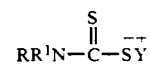

where R and R$^1$ are the same or different aliphatic or aromatic hydrocarbyl group having 1 to 40 carbon atoms or at least one heteroatom which can be oxygen, sulfur or nitrogen and can contain phenyl, naphthyl or anthryl substituents or can be a (CHn)m group which is part of an alicyclic or heterocyclic system such as pyrrole, pyrrolidine, piperidine, or morpholine, n is 1 or 2 and m is 2 to 8. Y is an ammonium or metal radical. Metal radicals include metals selected from group IA of the Periodic Table of the Elements (Sargent-Welch Scientific Company, 1980). Preferred amine dithiocarbamate salts are the salts of N,N-di-2-ethylhexyl-dithiocarbamic acid, N,N-didodecyldithiocarbamic acid and N,N-dibutyldithiocarbamic acid. Appropriate metal salts include the sodium or potassium salts of N,N-diorganodithiocarbamic acids which are derived from sodium or potassium hydroxide. The metal or amine dithiocarbamate salts are obtained by reacting a secondary amine with carbon disulfide and either a metal hydroxide (to form the metal dithiocarbamate salts) or a tertiary amine (to form the amine dithiocarbamate salts) in the presence of an aprotic solvent such as hexane, toluene or benzene. The reactants will react in approximately stoichiometric proportions to form the salt, preferably, the reaction is carried out in proportion expressed as molar ratio of carbon disulfide to tertiary amine or metal hydroxide of 1:1. The reactants can be contacted at ambient pressure and temperature. The reaction temperature should be maintained in a temperature range between 0° C. and 50° C., preferably, below 35° C. The reactants can be contacted for approximately 5 minutes to 48 hours, preferably 1–3 hours.

The tertiary amines for obtaining the salts of the present invention are those having the structural formula:

where R', R" and R''' are the same or different aliphatic hydrocarbyl radicals containing 1 to 12 carbon atoms or at least one heteroatom which can be oxygen sulfur or nitrogen. The preferred amine is triethyl amine. Mixtures of amines can also be used, a preferred mixture being a 1:1 mixture of the foregoing amines. Alternatively, as mentioned above, metal hydroxides such as sodium hydroxide and potassium hydroxide can be used.

The resulting diorganodithiocarbamate salts are reacted with organic oxides to obtain the desired hydroxyalkyl esters. Suitable organic oxides are hydrocarbylene oxides having the structural formula:

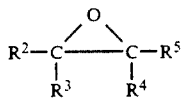

where $R^2$, $R^3$, $R^4$ and $R^5$ are the same or different, hydrogen atom or hydrocarbyl, containing 1 to 30 atoms, preferably, carbon or at least one heteroatom which can be oxygen, sulfur or nitrogen. The hydrocarbyl can be alkyl or aryl. Preferred oxides are ethylene oxide, styrene oxide, propylene oxide, butylene oxide, 1,2-epoxytetradecane, 1,2-epoxyhexadecane, 1,2-epoxyoctadecane and the like. Mixtures of oxides can also be used, a preferred mixture being a 1:1 mixture of oxides. The resulting esters have the following general structural formula:

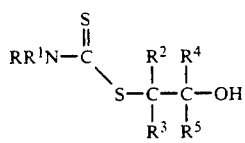

where R, $R^1$, $R^2$, $R^3$, $R^4$ and $R^5$ are as defined above. The esters are formed by contacting the diorganodithiocarbamate salts with organic oxides at ambient pressure. The temperature can be maintained from 0° C. to 100° C., preferably, below 45° C. The reactants can be contacted for approximately 5 minutes to 48 hours, preferably, 1-2 hours.

The esters of the present invention can be borated by known boration methods. Typically, the hydroxyester is reacted with boric acid in a suitable solvent at temperatures ranging from 90° C. to 300° C. at ambient pressure to yield boron-containing products. Specific reaction conditions and molar equivalents of the reactants are well known. Partial or complete boration can be used to impart the beneficial characteristics. An excess of a boron-containing borating reagent can be used. More complete boration is preferred. The products can contain from 0.01% to 10% boron or more, preferably, at least 0.5% boron. Boration is not limited to the boric acid method, any convenient method of boration known in the art can be used. For example, transesterification can be undertaken using a trihydrocarbyl borate such as tributyl borate at reaction temperatures of up to 270° C. Other borating agents may be used such as boron oxide, metaborate dihydrocarbyl borates, i.e. dibutyl borate and trihydrocarbyl borates, i.e. tributyl borate. In the boration procedure for making the products of the present invention, the hydroxyalkyl esters are reacted with boric acid in a stoichiometric amount, less than stoichiometric amount or an excess of up to 1,000% of boric acid or other convenient borating agent. A solvent or diluent inert to the reactants can also be used to facilitate reaction. The preferred solvents being xylenes, toluene, benzene or hexane. It is believed that the following structural formula represents a general structure for the borated esters of the present invention.

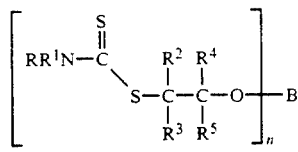

where R, $R^1$, $R^2$, $R^3$, $R^4$ and $R^5$ are as defined above and n is an integer.

The borated esters of dithiocarbamic acids can be effectively used in mineral oil, synthetic oils and mixtures thereof and greases made from the foregoing oils. Specifically contemplated for use with the additives of the present invention are liquid hydrocarbon oils of any suitable lubricating viscosity. Also, the additives are designed to be appropriate in automotive engine oils, marine diesel oils, aviation lubricants, automotive fluids such as brake fluids, power brake fluids, transmission fluids, power steering fluids, hydraulic fluids, industrial gear oils and greases for industrial high temperature operation and in liquid hydrocarbon fuels.

A significant feature of the present invention is that the products are metal-free and, therefore, are believed to present a toxicologically desirable additive.

It is contemplated that the borated reaction products of the present invention can also be added to plastic materials and fuel compositions which are similarly susceptible to oxidative deterioration.

It is to be understood that the compositions contemplated herein can also contain other additive materials. For example, ashless detergents, dispersants, co-antioxidants, co-friction modifiers, co-load carrying agents, corrosion inhibitors, pour point depression agents, color stabilizers and antifoam agents. These are exemplified by phenates, sulfonates, esters, oxides, trioxides, dithiophosphates, metallic acrylates, detergents, amines, phosphates, phosphites, heterocyclic compounds and the like. Also included are polymeric acrylates, ethylene-propylene copolymers, styrene-diene polymers and similar materials.

In instances where synthetic oils are preferred for use alone or in blends of synthetic oils and mineral oil or as the base for greases, suitable synthetic materials include polyisobutylene, polybutenes, hydrogenated polydecenes, polypropylene glycol, polyethylene glycol, trimethylol propane esters, neopentyl and pentaerythritol esters of carboxylic acids, di(2-ethylhexyl) sebacate, di(2-ethylhexyl) adipate, dibutyl phthalate, fluorocarbons, silicate esters, silane, esters of phosphorous-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis(p-phenoxy phenyl)ether, phenoxy phenylethers, dialkylbenzenes, etc.

When the additive is blended with greases, mineral oils falling within the range of from 60 SSU to 6,000 SSU at 100° F. may be used. The greases are usually made from the lubricating oil combined with a grease forming quantity of a thickening agent. A wide variety of materials can be used to impart the desired consistency of the grease. Examples of thickening materials include metal soaps, and non-soap thickeners, such as surface-modified clays and silicas, aryl ureas, calcium complexes and similar materials. In general, grease thickeners are employed which do not melt or dissolve when used at the required temperature within a particular environment. However, any material which is normally employed for thickening or gelling oleaginous fluids or forming greases may be used.

Among other classes of thickening agents which work well with the invention, when it is to be used in a grease formulation, contain at least a portion of alkali metal, alkali earth metal or amine soaps of hydroxy-containing fatty acids, fatty glycerides and fatty esters such as methyl esters having from 12 to 30 carbon atoms per molecule. The particularly preferred members of the foregoing acids and fatty materials are hydroxy-containing soap thickeners such as 12-hydroxy stearic acid, glycerides and methyl esters containing 12-hydroxystearates, 14-hydroxystearic acid, 16-hydroxystearic acid-and 6-hydroxystearic acid. The metals are typified by sodium, lithium, calcium and barium. A preferred metal thickener is lithium.

Although the additive alone has good thermal/oxidative stability when blended with greases containing any of the above-mentioned thickeners, often minor additional amounts of a source of phosphorus and sulfur moieties can produce even better overall thermal/oxidative stability when used in conjunction with the dithiocarbamate derived borated additive in a grease thickened with any one of the above-mentioned hydroxy-carboxylate soap thickeners. Both of these can be present in the same molecule, such as in a metal or non-metal phosphorodithioate of the formula

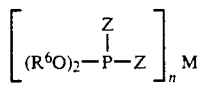

wherein $R^6$ is a hydrocarbyl group containing 3 to 18 carbon atoms or mixtures thereof. $R^6$ can also be a hydroxyl-containing or ester-containing hydrocarbyl group or may additionally contain sulfur, at least one Z containing sulfur. M is preferably a metal, but may be a non-metal, such as one of these mentioned hereunder, n is the valence of M and Z is oxygen or sulfur, at least one Z being sulfur. The phosphorodithioate can also be derived from diols such as 1,2-dodecanediol, 1,3-pentanediol and similar $C_4$-$C_{20}$ diols and mixtures. The phosphorodithioate can also be complexed as a zinc acetate complexed zinc phosphorodithioate.

In this compound, $R^6$ is preferably an alkyl group and may be a propyl, butyl, pentyl, hexyl, octyl, decyl, dodecyl, tetradecyl or octadecyl group, including those derived from isopropanol, propanol, butanol, isobutanol, sec-butanol, 4-methyl-2-pentanol, 2-ethylhexanol, oleyl alcohol and mixtures thereof. Further included are alkaryl groups such as butylphenyl, octylphenyl, nonylphenyl and dodecylphenyl groups.

The metals embraced by M include those in Groups IA, IIA, IIB, and VIII of the Periodic Table. Representative examples are lithium, sodium, calcium, zinc, cadmium, silver, gold and molybdenum. Non-metallic ions include organic groups derived from vinyl esters such as vinyl acetate, vinyl ethers such as butyl vinyl ether and epoxides such as propylene oxide and 1,2-epoxydodecane. The non-metallic ions may also be derived from nitrogenous compounds such as those derived from hydrocarbyl amines and diamines, including oleylamine and N-oleyl-1,3-propylenediamine, the imidazolines and oxazolines.

The phosphorus and sulfur can also be supplied from the combination of two separate compounds, such as the combination of (1) a dihydrocarbyl phosphite having 2 to 10 carbon atoms in each hydrocarbyl group or mixtures of phosphites and (2) a sulfide such as sulfurized isobutylene, dibenzyl disulfide, sulfurized terpenes, phosphorodithionyl disulfide and sulfurized jojoba oil. The phosphites include the dibutyl, dihexyl, dioctyl, didecyl and similar phosphites. Phosphate esters containing 4 to 20 carbon atoms in each hydrocarbyl group, such as tributyl phosphate, tridecyl phosphate, tricresyl phosphate and mixtures of such phosphates, can be used. Additionally, compounds containing both sulfur and phosphorus can be used such as phosphorodithionyl disulfide. A minor suitable amount of the phosphorus and sulfur moiety ranges from 0.01 to 10 wt. %, preferably 0.2 to 3 wt. % based on the total weight of the composition.

The lubricants and greases of the present invention contain a minor amount of the additive to impart the desired degree of multifunctional antioxidant, load carrying and friction modifying properties. Generally, this amount is in the range of 0.01 wt.% to about 10.0 wt.%, preferably about 0.03 wt% to 1.0 wt% of the total weight of the lubricant.

EXAMPLE 1

Bis-(2-ethylhexyl) amine, 121 g (0.5 moles), triethylamine, 60 g (0.6 moles), and toluene, 150 ml were charged into a 1-liter reaction flask. To the well-stirred mixture at ambient temperature, carbon disulfide, 45 g (0.6 moles), was added slowly, dropwise, keeping the exothermic reaction temperature below 35° C.

To the triethylammonium salt of the N,N-di-(2-ethylhexyl) dithiocarbamic acid thus formed, was added 120 g of propylene oxide, dropwise, at ambient temperature, maintaining the exothermic reaction temperature below 45° C. After the addition and the exothermic reaction had subsided, the reaction mixture was heated briefly (1 hour) at 65° C. and then cooled to ambient temperature.

Boric acid, 60 g, was charged into the reaction mixture, a Dean Stark trap was attached to the reaction flask, and the reaction mixture was then slowly heated to reflux temperature. The resulting foaming was moderated by reducing the speed of stirring and occasionally lowering the reaction temperature. The heating was stopped when no more water was collected in the Dean Stark trap. It may not be necessary to perform the reaction to completion but completion is often preferred. After cooling to ambient temperature, the reaction mixture was diluted with 100 ml of toluene, filtered over celite and the filtrate stripped of solvent to give 216.2 g of a clear liquid product.

Following the procedure of Example 1 but varying the olefin oxides and/or the secondary amine, the products of the examples given below were obtained mostly in quantitative yields.

EXAMPLE 2

From bis-(2-ethylhexyl) amine and stoichiometric amounts of styrene oxide as the reactant secondary amine and olefin oxide, respectively, the product of this example was obtained following the procedure of Example 1.

EXAMPLE 3

Product was obtained, following the procedure of Example 1, using a stoichiometric amount of dibutylamine and propylene oxides as the reactant secondary amine and olefin oxide, respectively.

EXAMPLE 4

Same reaction as Example 3, except that a stoichiometric amount of styrene oxide was used as the olefin oxide.

EXAMPLE 5

Same as Example 4, except that a stoichiometric amount of Viking Chemical Co. Vikolox 14 brand of 1,2-epoxytetradecane was used as the olefin oxide.

EXAMPLE 6

Product was obtained, following the procedure of Example 1, from di-(dodecyl)amine and a stoichiometric amount of styrene oxide.

EXAMPLE 7

Same as Example 6 except that the reactant olefin oxide was propylene oxide.

EVALUATION OF PRODUCT

The additives prepared in the foregoing examples were blended in a concentration of 1% in a neutral base stock oil and tested for antioxidant and antiwear performance. The antioxidant effectiveness was measured in the B-10 Catalytic Oxidation Test and the antiwear performance was measured in the Shell 4-Ball Wear Test.

In the B-10 Catalytic Oxidation Test the test lubricant was subjected to a stream of air which was bubbled through a volume of the test composition at a rate of about 5 liters per hour at 325° F. for 40 hours. Present in the composition in addition to the additive, in a 1% concentration in the base oil, were metals frequently used as materials to construct engines such as:

(a) 15.6 square inches of sand-blasted iron wire;
(b) 0.78 square inches of polished copper wire;
(c) 0.87 square inches of polished aluminum wire; and
(d) 0.107 square inches of polished lead surface. The results of this test were represented in terms of change in kinematic viscosity (KV), neutralization number (NN) and lead loss. Essentially the small change in kinematic viscosity meant that the lubricant maintained its internal resistance to oxidation under high temperatures, a small change in neutralization number indicates that the oil maintained its acidity level under oxidizing conditions and the little to no change in lead loss indicated that the lubricant was not corrosive to lead under corrosive conditions.

In the 4-Ball Wear Test for scarring 52100 stainless steel balls of ½ inch in diameter were applied under a 60 Kg load for 30 minutes at 2000 RPM and 200° F. The results of the test were reported in Table 2. Following the Standard ASTM testing procedure, three of the stainless steel balls were placed in a container. The test lubricants were each added to the container and a chuck mounted on a device spinned a fourth ball, which was positioned above and in contact with the other three stationary balls, at 2000 RPM under 60K of load for 30 minutes at 200° F. From the reported data it will be noted that the additives of the present invention exhibited good antiwear performance under the severe testing conditions.

TABLE 1

B-10 CATALYTIC OXIDATION TEST
325° F., 40 Hours

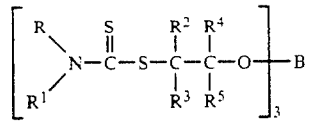

| Item | Additive (1% Concentration) | Acidity Incr $\Delta$NN | % Vis Incr % $\Delta$KV | Pb Loss mg |
|---|---|---|---|---|
| base oil | None | 17.6 | 142.8 | 8.5 |
| 1 | $R, R^1 = C_8H_{17}$; $R^2, R^3, R^4 = H$; $R^5 = CH_3$ | 1.2 | 14.5 | 0.0 |
| 2 | $R, R^1 = C_8H_{17}$; $R^2, R^3, R^4 = H$; $R^5 = C_6H_5$ | 2.6 | 24.2 | 0.3 |
| 3 | $R, R^1 = C_4H_9$; $R^2, R^3, R^4 = H$; $R^5 = CH_3$ | 4.1 | 31.5 | 0.4 |
| 4 | $R, R^1 = C_4H_9$; $R^2, R^3, R^4 = H$; $R^5 = C_6H_5$ | 4.1 | 34.9 | 0.2 |
| 5 | $R, R^1 = C_4H_9$; $R^2, R^3, R^4 = H$; $R^5 = C_{12}H_{25}$ | 6.6 | 40.8 | 0.3 |
| 6 | $R, R^1 = C_{12}H_{25}$; $R^2, R^3, R^4 = H$; $R^5 = C_6H_5$ | 4.8 | 41.1 | 0.0 |
| 7 | $R, R^1 = C_{12}H_{25}$; $R^2, R^3, R^4 = H$; $R^5 = CH_3$ | 6.2 | 68.5 | 0.0 |

TABLE 2

4-BALL WEAR TEST
½" BALLS, S2100 STEEL, 2000 RPM, 60 KG, 200° F., 30 MIN

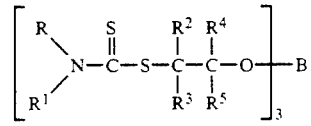

| Item | Additive (1% Concentration) | Wear Scar Diam. (mm) |
|---|---|---|
| Base Oil | None | 3.7 |
| 1 | $R = R^1 = C_8H_{17}$; $R^2, R^3, R^4 = H$; $R^5 = CH_3$ | 0.6 |
| 2 | $R = R^1 = C_8H_{17}$; $R^2, R^3, R^4 = H$; $R^5 = C_6H_5$ | 0.7 |
| 3 | $R = R^1 = C_4H_9$; $R^2, R^3, R^4 = H$; $R^5 = CH_3$ | 0.7 |
| 4 | $R = R^1 = C_4H_9$; $R^2, R^3, R^4 = H$; $= C_6H_5$ | 0.9 |
| 5 | $R = R^1 = C_4H_9$; $R^2, R^3, R^4 = H$; $R^5 = C_{12}H_{25}$ | 1.6 |
| 6 | $R = R^1 = C_{12}H_{25}$; $R^2, R^3, R^4 = H$; $R^5 = C_6H_5$ | 0.7 |
| 7 | $R = R^1 = C_{12}H_{25}$; $R^2, R^3, R^4 = H$; $R^5 = CH_3$ | 1.6 |

The additive of the present invention was evaluated for its additive performance in greases in the ASTM D2265 Standard Method Test for Dropping Point of Lubricating Greases of Wide Temperature Range. Grease samples were formulated by blending a low concentration of the product of Examples 1, 3 and 5 with a lubricating grease thickened with a conventional lithium hydroxystearate grease thickener. The dropping point test determined the temperature at which a grease passed from a semi-solid state to a liquid state under the conditions of the test, thus, loosing its gel form. The dropping point also reflected the thermal and oxidative stability of the grease. The test grease was placed in a cup equipped with a thermometer. The grease cup was placed in a test tube, and the entire assembly was placed in an oven. The temperature was gradually increased. When a drop of material fell from the cup, the temperature was recorded. The dropping point of each grease sample was calculated, and the results were reported in Table 3.

TABLE 3

Lithium Hydroxystearate Grease Evaluation
Dropping Point of Lubricant Grease
D2265-650° F. Oven $$\left[ \begin{array}{c} R \\ \diagdown \\ N-C-S-C-C-O \\ \diagup \\ R^1 \end{array} \begin{array}{c} S \\ \| \\ \end{array} \begin{array}{cc} R^2 & R^4 \\ | & | \\ | & | \\ R^3 & R^5 \end{array} \right]_3 B$$

| Item | Additive | % Additive Conc | Dropping Point(°F.) |
|---|---|---|---|
| Base Grease | None | 0 | 410 |
| 1 | R, R$^1$ = C$_8$H$_{17}$; R$^2$, R$^3$, R$^4$ = H; R$^5$ = CH$_3$ (in base grease) | 1 | 460 |
|  |  | 2 | 460 |
| 3 | R, R$^1$ = C$_4$H$_9$; R$^2$, R$^3$, R$^4$ = H; R$^5$ = CH$_3$ (in base grease) | 1 | 473 |
|  |  | 2 | 477 |
| 5 | R, R$^1$ = C$_4$H$_9$; R$^2$, R$^3$, R$^4$ = H; R$^5$ = C$_{12}$H$_{25}$ (in base grease) | 1 | 430 |
|  |  | 2 | 430 |

As the Dropping Point Test results show, these metal-free, ashless additives increased the dropping point of the grease formulation, thereby improving the thermal and oxidative properties of the grease. Further, because greases blended with the additives of the present invention had high dropping points, they remained in a semisolid state at temperatures greater than the base grease. This meant that the grease formulations containing the instant additives were useful at higher temperatures than the grease formulation that did not contain the additive.

What is claimed is:

1. A reaction product for blending with a lubricant having multifunctional antioxidant, load carrying and friction modifying properties comprising the borated reaction product of an amine or metal dithiocarbamate salt and an organic oxide; the dithiocarbamate salt having the structural formula:

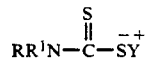

where R and R$^1$ are the same or different hydrocarbyl groups having 1 to 40 carbon atoms and Y is a metal or ammonium radical and the organic oxide having the structural formula

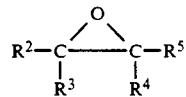

where R$^2$, R$^3$, R$^4$ and R$^5$ are the same or different, hydrogen or hydrocarbyl groups containing 1 to 30 carbon atoms said hydrocarbyl groups optionally containing at least one heteroatom selected from the group consisting of oxygen, sulfur and nitrogen.

2. The reaction product of claim 1 in which R and R$^1$ contain at least one heteroatom which is oxygen, sulfur or nitrogen bonded to aromatic or aliphatic hydrocarbyl radicals containing phenyl, naphthyl or anthryl substituents or are both (CHn)m comprising part of an alicyclic or heterocyclic system selected from the group consisting of pyrrole, pyrrolidine, morpholine and piperidine where n is 1 to 2 and m is 2 to 8.

3. The reaction product of claim 1 in which the dithiocarbamate salt is the salt of N,N-di-(2-ethylhexyl)dithiocarbamic acid, N,N-didodecyldithiocarbamic acid or N,N-dibutyldithiocarbamic acid.

4. The reaction product of claim 1 in which the oxide is ethylene oxide, styrene oxide, propylene oxide, butylene oxide, 1,2-epoxyhexadecane, 1,2-epoxyoctadecane or 1,2-epoxytetradecane or mixture thereof.

5. The reaction product of claim 1 in which the amine or the metal dithiocarbamic salt and the organic oxide are reacted at a temperature ranging from 20° C. to 100° C.

6. The reaction product of claim 1 in which the reaction product is borated with boric acid, boron oxide, metaborate, dihydrocarbyl borates or trihydrocarbyl borates.

7. A lubricating composition comprising a major amount of a lubricating oil or grease and a minor amount of a multifunctional antioxidant, load carrying and friction modifying borated reaction product of an amine or metal dithiocarbamic salt having the structural formula:

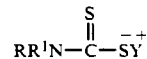

where R and R$^1$ are the same or different hydrocarbyl groups having 1 to 40 carbon atoms and Y is a metal or ammonium radical with an organic oxide having the structural formula:

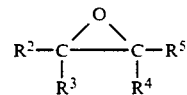

where R$^2$, R$^3$, R$^4$ and R$^5$ are the same or different, hydrogen or hydrocarbyl groups containing 1 to 30 carbon atoms said hydrocarbyl groups optionally containing at least one heteroatom selected from the group consisting of oxygen, sulfur and nitrogen.

8. The composition of claim 7 in which R, and R$^1$ are hydrocarbyl in which each have from 1 to 40 carbon atoms or are hydrocarbyl which contains at least one heteroatom which is oxygen, sulfur or nitrogen bonded to aromatic or aliphatic hydrocarbyl radicals containing phenyl, naphthyl or anthryl substituents or are both (CHn)m comprising part of an alicyclic or heterocyclic system selected from the group consisting of pyrrole, pyrrolidine, morpholine and piperidine where n is 1 to 2 and m is 2 to 8.

9. The composition of claim 7 in which the dithiocarbamate salt is the salt of N,N-di-(2-ethylhexyl)dithiocarbamic acid, N,N-didodecyldithiocarbamic acid or N,N-dibutyldithiocarbamic acid.

10. The composition of claim 7 in which the oxide is ethylene oxide, styrene oxide, propylene oxide, butyleneoxide, 1,2-epoxyhexadecane, 1,2-epoxyoctadecane or 1,2-epoxytetradecane or mixture thereof.

11. The composition of claim 7 in which the amine or the metal dithiocarbamic salt and the organic oxide are reacted at a temperature ranging from 0° C. to 100° C.

12. The composition of claim 7 in which the reaction product is borated with boric acid, boron oxide, metaborate, dihydrocarbyl borates or trihydrocarbyl borates.

13. The composition of claim 7 in which the grease is thickened with a hydroxy-containing soap thickener.

14. The composition of claim 13 in which the grease contains a minor amount of a source of phosphorus and sulfur moieties.

15. The composition of claim 7 in which the borated reaction product is blended with the lubricant or grease in an amount of 0.01 wt% to about 10.0 wt% of the total weight of the composition.

16. A method of making a lubricating composition comprising blending with a major proportion of a lubricating oil or grease a multifunctional antioxidant, load carrying and friction modifying amount of a borated reaction product of an amine or metal dithiocarbamate salt having the structural formula:

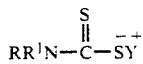

where R and $R^1$ are the same or different hydrocarbyl group having 1 to 40 carbon atoms and Y is a metal or ammonium radical and an organic oxide having the structural formula:

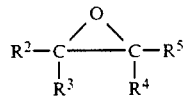

where $R^2$, $R^3$, $R^4$ and $R^5$ are the same or different, hydrogen or hydrocarbyl groups having 1 to 30 carbon atoms containing at least one heteroatom selected from the group consisting of oxygen, sulfur and nitrogen.

17. The method of claim 16 in which R and $R_1$ are hydrocarbyl which have from 1 to 40 carbon atoms or are hydrocarbyl which have from 1 to 40 carbon atoms or are hydrocarbyl which contain at least one heteroatom which is oxygen, sulfur or nitrogen bonded to aromatic or aliphatic hydrocarbyl radicals containing phenyl, naphthyl or anthryl substituents or are both $(CH_n)_m$ comprising part of an alicyclic or heterocyclic system selected from the group consisting of pyrrole, pyrrolidine, morpholine and piperidine where n is 1 to 2 and m is 2 to 8.

18. The method of claim 16 in which the dithiocarbamate salt is the salt of N,N-di-(2-ethylhexyl)dithiocarbamic acid N,N-didodecyldithiocarbamic acid or N,N-dibutyldithiocarbamic acid.

19. The method of claim 16 in which the oxide is ethylene oxide, styrene oxide, propylene oxide, butylene oxide, 1,2-epoxyhexadecane, 1,2-epoxyoctadecane or 1,2-epoxytetradecane or mixture thereof.

20. The method of claim 16 in which the amine or the metal dithiocarbamic salt and the organic oxide are reacted at a temperature ranging from 0° C. to 100° C.

21. The method of claim 16 in which the reaction product is borated with boric acid, boron oxide, metaborate, dihydrocarbyl borates, or trihydrocarbyl borates.

22. The method of claim 16 in which the reaction product is blended with the lubricating oil or grease in an amount of 0.01 wt% to 10 wt. % of the total weight of the composition.

23. The method of claim 16 in which the grease is thickened with a hydroxy-containing soap thickener.

24. The method of claim 23 in which the grease contains a minor amount of a source of phosphorus and sulfur moieties.

25. The composition of claim 14 in which the grease contains a minor amount of a metal or non-metal dithiophosphate.

26. The composition of claim 13 in which the hydroxy-containing soap thickener is a hydroxycarboxylate soap thickener.

* * * * *